United States Patent
Groden et al.

(10) Patent No.: US 11,921,507 B2
(45) Date of Patent: Mar. 5, 2024

(54) VEHICLE SYSTEM AND METHOD FOR PROVIDING SERVICES

(71) Applicant: Skyryse, Inc., El Segundo, CA (US)

(72) Inventors: Mark Groden, Marina Del Rey, CA (US); Mitch Adler, Hawthorne, CA (US); Nur Harell, Hawthorne, CA (US)

(73) Assignee: Skyryse, Inc., El Segundo, CA (US)

( * ) Notice: Subject to any disclaimer, the term of this patent is extended or adjusted under 35 U.S.C. 154(b) by 0 days.

(21) Appl. No.: 17/551,595

(22) Filed: Dec. 15, 2021

(65) Prior Publication Data

US 2022/0107640 A1 Apr. 7, 2022

Related U.S. Application Data

(63) Continuation of application No. 16/695,747, filed on Nov. 26, 2019, now Pat. No. 11,256,256, which is a
(Continued)

(51) Int. Cl.
*G05D 1/00* (2006.01)
*A61G 3/00* (2006.01)
(Continued)

(52) U.S. Cl.
CPC .......... *G05D 1/0088* (2013.01); *A61G 3/001* (2013.01); *B64C 39/024* (2013.01); *B64D 45/00* (2013.01);
(Continued)

(58) Field of Classification Search
CPC .. G05D 1/0088; G05D 1/0202; G05D 1/0676; B64F 5/60; B64F 1/18;
(Continued)

(56) References Cited

U.S. PATENT DOCUMENTS 3,455,182 A 7/1969 Kelley
3,747,877 A 7/1973 Drew
(Continued)

FOREIGN PATENT DOCUMENTS

CN 103942454 A 7/2014
CN 106094841 A 11/2016
(Continued)

OTHER PUBLICATIONS

China National Intellectual Property Administration, Office Action, CN Patent Application No. 201880008254.4, dated Nov. 30, 2021, 30 pages.
(Continued)

*Primary Examiner* — Gertrude Arthur Jeanglaude
(74) *Attorney, Agent, or Firm* — Fenwick & West LLP

(57) ABSTRACT

A method for providing medical services to a patient, including: receiving a medical service request associated with a patient location; selecting an aircraft, located at an initial location, from a plurality of aircraft based on the patient location and the initial location; determining a flight plan for flying the aircraft to a region containing the patient location; at a sensor of the aircraft, sampling a first set of flight data; at a processor of the aircraft, autonomously controlling the aircraft to fly based on the flight plan and the set of flight data; selecting a landing location within the region; and landing the aircraft at the landing location, including: sampling a set of landing location data; determining a safety status of the landing location based on the set of landing location data; outputting a landing warning observable at the landing location; at the sensor, sampling a second set of flight data; and in response to determining the safety status and outputting the landing warning, autonomously controlling the aircraft to land at the landing location based on the second set of flight data.

20 Claims, 6 Drawing Sheets

Related U.S. Application Data continuation of application No. 15/934,162, filed on Mar. 23, 2018, now Pat. No. 10,528,050, which is a continuation of application No. 15/661,763, filed on Jul. 27, 2017, now Pat. No. 10,185,320, which is a continuation of application No. 15/643,205, filed on Jul. 6, 2017, now Pat. No. 9,849,044.

(60) Provisional application No. 62/469,419, filed on Mar. 9, 2017, provisional application No. 62/452,051, filed on Jan. 30, 2017.

(51) Int. Cl.

| | |
|---|---|
| B64C 39/02 | (2023.01) |
| B64D 45/00 | (2006.01) |
| B64D 45/04 | (2006.01) |
| B64D 45/08 | (2006.01) |
| B64F 1/18 | (2006.01) |
| B64F 5/60 | (2017.01) |
| G06Q 10/047 | (2023.01) |
| G06Q 10/0832 | (2023.01) |
| G06Q 50/22 | (2018.01) |
| G06Q 50/30 | (2012.01) |
| G07C 5/00 | (2006.01) |
| G08G 5/00 | (2006.01) |
| G16H 40/20 | (2018.01) |
| B64U 10/10 | (2023.01) |
| G06V 20/52 | (2022.01) |
| G08B 7/06 | (2006.01) |
| G16H 15/00 | (2018.01) |

(52) U.S. Cl.
CPC .............. *B64D 45/04* (2013.01); *B64D 45/08* (2013.01); *B64F 1/18* (2013.01); *B64F 5/60* (2017.01); *G05D 1/0202* (2013.01); *G05D 1/0676* (2013.01); *G06Q 10/047* (2013.01); *G06Q 10/0832* (2013.01); *G06Q 50/22* (2013.01); *G06Q 50/30* (2013.01); *G07C 5/008* (2013.01); *G08G 5/0013* (2013.01); *G08G 5/003* (2013.01); *G08G 5/0034* (2013.01); *G08G 5/0056* (2013.01); *G08G 5/0091* (2013.01); *G08G 5/0095* (2013.01); *G16H 40/20* (2018.01); *A61G 2220/10* (2013.01); *B64D 2045/0085* (2013.01); *B64U 10/10* (2023.01); *B64U 2201/10* (2023.01); *B64U 2201/20* (2023.01); *G06V 20/52* (2022.01); *G08B 7/06* (2013.01); *G16H 15/00* (2018.01)

(58) Field of Classification Search
CPC ...... G16H 40/20; A61G 3/001; B64C 39/024; B64D 45/00; B64D 45/04; B64D 45/08; G06Q 10/047; G06Q 50/30; G07C 5/008; G08G 5/0013; G08G 5/003; G08G 5/0034; G08G 5/0056; G08G 5/0091; G08G 5/0095; G08B 7/06
See application file for complete search history.

(56) References Cited

U.S. PATENT DOCUMENTS

| | | |
|---|---|---|
| 3,995,793 A | 12/1976 | Wing |
| 4,138,077 A | 2/1979 | Okumura |
| 4,500,966 A | 2/1985 | Zagranski et al. |
| 4,676,457 A | 6/1987 | Allen |
| 4,709,881 A | 12/1987 | Rafikian et al. |
| 4,957,121 A | 9/1990 | Icenogle et al. |
| 5,403,155 A | 4/1995 | Head et al. |
| 5,493,309 A | 2/1996 | Bjornholt |
| 6,115,373 A | 9/2000 | Lea |
| 6,739,556 B1 | 5/2004 | Langston |
| 6,775,373 B2 | 8/2004 | Stoughton |
| 6,776,373 B1 | 8/2004 | Talmage |
| 7,032,860 B1 | 4/2006 | Kirk et al. |
| 7,059,570 B2 | 6/2006 | Strong |
| 7,143,973 B2 | 12/2006 | Ballew |
| 7,377,468 B2 | 5/2008 | Saggio et al. |
| 7,458,544 B1 | 12/2008 | Sarigul-Klijn et al. |
| 7,487,939 B1 | 2/2009 | Christof |
| 7,499,713 B2 * | 3/2009 | Gasbarro ............ A61B 5/1112 455/414.1 |
| 7,523,892 B2 | 4/2009 | Cook |
| 7,611,090 B2 | 11/2009 | Oleshchuk et al. |
| 8,018,079 B2 | 9/2011 | Kelly |
| 8,033,507 B2 | 10/2011 | Fox |
| 8,399,816 B2 | 3/2013 | Glasson |
| 8,453,962 B2 | 6/2013 | Shaw |
| 8,521,340 B2 | 8/2013 | Coulmeau |
| 8,868,258 B2 | 10/2014 | Papadopoulos et al. |
| 8,909,391 B1 | 12/2014 | Peeters |
| 8,948,935 B1 | 2/2015 | Peeters et al. |
| 8,979,031 B2 | 3/2015 | Fox |
| 8,979,032 B1 | 3/2015 | Hester et al. |
| 9,051,043 B1 | 6/2015 | Peeters et al. |
| 9,158,304 B2 | 10/2015 | Fleck |
| 9,199,742 B2 | 12/2015 | Giannakopoulos |
| 9,257,048 B1 | 2/2016 | Offer et al. |
| 9,308,970 B1 | 4/2016 | Gefken et al. |
| 9,310,222 B1 | 4/2016 | Suiter et al. |
| 9,319,913 B2 | 4/2016 | Raleigh et al. |
| 9,346,543 B2 | 5/2016 | Kugelmass |
| 9,346,544 B2 | 5/2016 | Kugelmass |
| 9,520,066 B2 | 12/2016 | Spinelli et al. |
| 9,522,598 B2 * | 12/2016 | Akula ............... A61B 5/7282 |
| 9,645,582 B2 | 5/2017 | Shue |
| 9,688,403 B2 | 6/2017 | Winn et al. |
| 9,786,187 B1 | 10/2017 | Bar-Zeev et al. |
| 9,849,044 B1 * | 12/2017 | Groden ............... G08G 5/0091 |
| 9,868,526 B2 | 1/2018 | Yates |
| 10,004,652 B1 | 6/2018 | Groden et al. |
| 10,185,320 B2 | 1/2019 | Groden et al. |
| 10,453,347 B2 | 10/2019 | Winkler |
| 10,515,416 B2 | 12/2019 | Winn et al. |
| 10,531,994 B2 | 1/2020 | Groden et al. |
| 2003/0094537 A1 | 5/2003 | Austen-Brown |
| 2005/0087652 A1 | 4/2005 | Holmboe |
| 2005/0127238 A1 | 6/2005 | Ballew |
| 2005/0139363 A1 | 6/2005 | Thomas |
| 2005/0201345 A1 * | 9/2005 | Williamson ........... G16H 40/63 370/338 |
| 2005/0230529 A1 | 10/2005 | Towne |
| 2005/0230555 A1 | 10/2005 | Strong |
| 2006/0032984 A1 | 2/2006 | Preston |
| 2006/0106506 A1 | 5/2006 | Nichols et al. |
| 2006/0208136 A1 | 9/2006 | Cook |
| 2007/0055434 A1 | 3/2007 | Kohlmann |
| 2007/0138345 A1 | 6/2007 | Shuster |
| 2007/0164167 A1 | 7/2007 | Bachelder et al. |
| 2007/0262203 A1 | 11/2007 | Saggio et al. |
| 2008/0167763 A1 | 7/2008 | Duranti et al. |
| 2009/0003281 A1 | 1/2009 | Panabaker |
| 2009/0008499 A1 | 1/2009 | Shaw |
| 2009/0105890 A1 | 4/2009 | Jones et al. |
| 2010/0108817 A1 | 5/2010 | Fox |
| 2010/0213718 A1 | 8/2010 | Kelly |
| 2010/0219987 A1 | 9/2010 | Isom et al. |
| 2011/0009053 A1 | 1/2011 | Anglin et al. |
| 2011/0035149 A1 | 2/2011 | McAndrew et al. |
| 2011/0264312 A1 | 10/2011 | Spinelli et al. |
| 2012/0011996 A1 | 1/2012 | Glasson |
| 2012/0228432 A1 | 9/2012 | Fox |
| 2013/0218374 A1 | 8/2013 | Lacko et al. |
| 2013/0221153 A1 | 8/2013 | Norsham et al. |
| 2013/0221159 A1 | 8/2013 | Giannakopoulos |
| 2014/0067164 A1 | 3/2014 | Papadopoulos et al. |
| 2014/0117148 A1 | 5/2014 | Dyrla et al. |
| 2014/0129951 A1 | 5/2014 | Amin et al. |

(56) References Cited

U.S. PATENT DOCUMENTS

| | | |
|---|---|---|
| 2014/0140871 A1 | 5/2014 | Grieser |
| 2014/0343765 A1 | 11/2014 | Suiter et al. |
| 2015/0148988 A1 | 5/2015 | Fleck |
| 2015/0203200 A1 | 7/2015 | Bye et al. |
| 2015/0323931 A1 | 11/2015 | Downey et al. |
| 2016/0052626 A1 | 2/2016 | Vander Mey |
| 2016/0055754 A1 | 2/2016 | Ling et al. |
| 2016/0107750 A1 | 4/2016 | Yates |
| 2016/0240091 A1 | 8/2016 | Thiele et al. |
| 2016/0253908 A1 | 9/2016 | Chambers et al. |
| 2016/0274577 A1 | 9/2016 | Heinonen |
| 2016/0318615 A1 | 11/2016 | Pick |
| 2016/0357192 A1 | 12/2016 | McGrew et al. |
| 2016/0378121 A1 | 12/2016 | Shue |
| 2017/0003681 A1 | 1/2017 | Ross et al. |
| 2017/0274994 A1 | 9/2017 | Eller et al. |
| 2017/0344707 A1* | 11/2017 | Patel ................... G08G 1/202 |
| 2017/0369160 A1 | 12/2017 | White et al. |
| 2018/0065738 A1 | 3/2018 | Lappos et al. |
| 2018/0129226 A1 | 5/2018 | Rogers et al. |
| 2018/0189717 A1* | 7/2018 | Cao ..................... G06Q 50/30 |
| 2018/0214324 A1 | 8/2018 | Groden et al. |
| 2018/0225976 A1 | 8/2018 | Rinehart et al. |
| 2018/0251122 A1 | 9/2018 | Golston et al. |

FOREIGN PATENT DOCUMENTS

| | | | |
|---|---|---|---|
| CN | 106155089 A | 11/2016 | |
| DE | 202004005540 U | * 7/2004 | ............ G08B 21/02 |
| FR | 3003844 A1 | 10/2014 | |
| WO | WO 2017/064717 A1 | 4/2017 | |

OTHER PUBLICATIONS

European Search Report, EP Patent Application No. 18744623.2, dated Dec. 22, 2020, nine pages.
PCT International Search Report and Written Opinion, PCT Application No. PCT/US18/19547, dated Jul. 20, 2018, 33 pages.
PCT International Search Report and Written Opinion, PCT Application No. PCT/US18/20149, dated May 16, 2018, seven pages.
PCT International Search Report and Written Opinion, PCT Application No. PCT/US18/43641, dated Nov. 21, 2018, 16 pages.
United States Office Action, U.S. Appl. No. 16/707,785, dated Apr. 13, 2021, seven pages.
United States Office Action, U.S. Appl. No. 15/934,162, dated Jun. 11, 2019, six pages.
United States Office Action, U.S. Appl. No. 15/661,763, dated Aug. 27, 2018, six pages.
United States Office Action, U.S. Appl. No. 16/695,747, dated Jul. 23, 2021, six pages.
United States Office Action, U.S. Appl. No. 16/695,747, dated Mar. 30, 2021, nine pages.
China National Intellectual Property Administration, Office Action, CN Patent Application No. 201880008254.4, dated Jun. 24, 2022, 22 pages.
China National Intellectual Property Administration, Office Action, CN Patent Application No. 201880008254.4, dated Dec. 30, 2022, 22 pages.
Li, Z., "The China Disaster and Emergency Medicine," Tianjin Science and Technology Press, Jul. 2014, vol. 1, pp. 224-225.

* cited by examiner

000
VEHICLE SYSTEM AND METHOD FOR PROVIDING SERVICES

CROSS-REFERENCE TO RELATED APPLICATIONS

This application is a continuation of co-pending U.S. patent application Ser. No. 16/695,747 filed Nov. 26, 2019, which is a continuation of U.S. patent application Ser. No. 15/934,162, filed Mar. 23, 2018, now bearing U.S. Pat. No. 10,528,050, which is a continuation of U.S. patent application Ser. No. 15/661,763, filed Jul. 27, 2017, now bearing U.S. Pat. No. 10,185,320, which is a continuation of U.S. patent application Ser. No. 15/643,205, filed Jul. 6, 2017, now bearing U.S. Pat. No. 9,849,044, which claims the benefit of U.S. Provisional Application No. 62/452,051, filed Jan. 30, 2017, and U.S. Provisional Application No. 62/469,419, filed Mar. 9, 2017, all of which are incorporated in their entirety by this reference.

TECHNICAL FIELD

This invention relates generally to the field of vehicles, and more specifically to a new and useful vehicle system and method for providing vehicle-related services.

BACKGROUND

Typical vehicle-related services, and especially aircraft-related services, rely on a human to operate the vehicle, which can increase operation costs and/or vehicle requirements. Thus, there is a need in the vehicle field to create a new and useful vehicle system and method for providing vehicle-based services.

DESCRIPTION OF THE PREFERRED EMBODIMENTS

Figure 1:
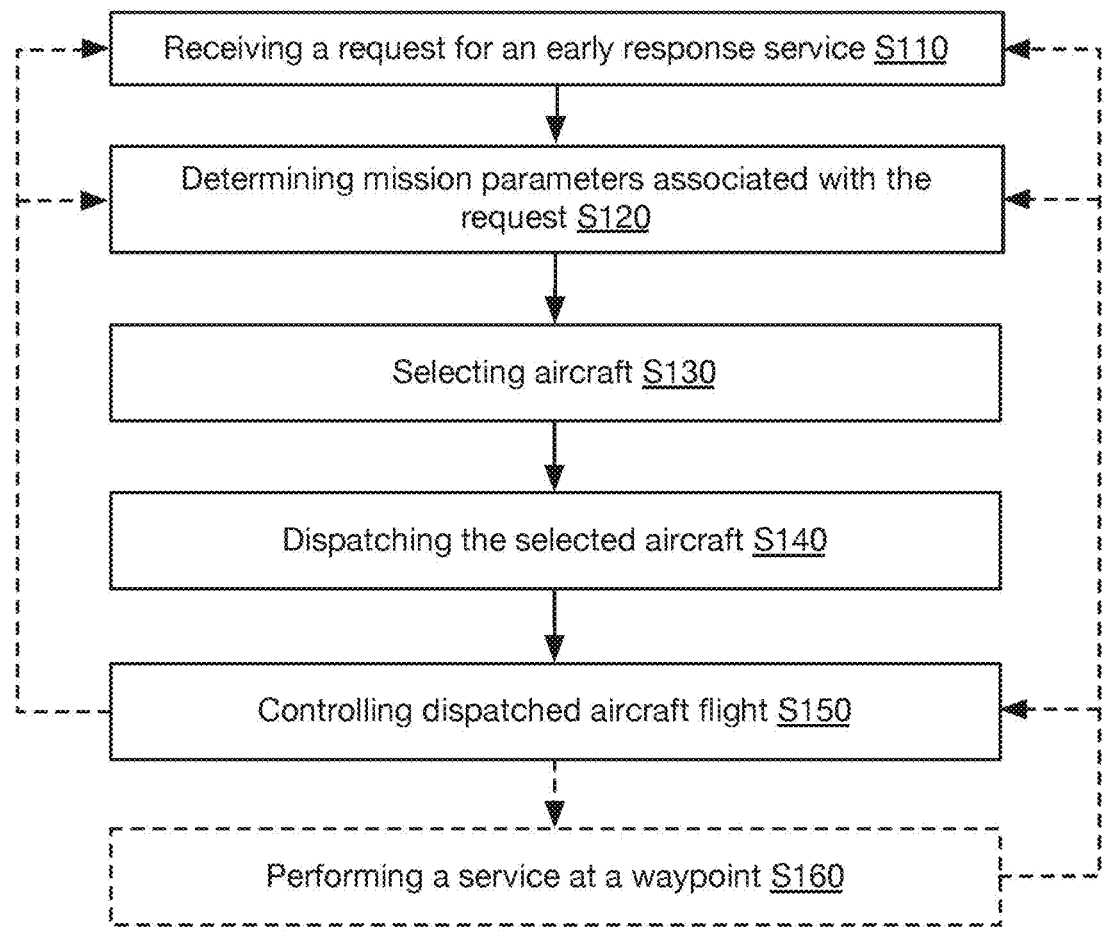
FIG. 1 is a flowchart diagram of the method for providing services.

The following description of the preferred embodiments of the invention is not intended to limit the invention to these preferred embodiments, but rather to enable any person skilled in the art to make and use this invention.

1. Overview

A method for providing services includes receiving a request for a service S110, determining mission parameters associated with the request S120, selecting aircraft S130 and/or other vehicle types, dispatching the selected aircraft S140 and/or other vehicle types, and controlling dispatched aircraft flight S150 and/or displaced vehicle travel, and can optionally include performing a service at a waypoint S160 and/or any other suitable elements. The method preferably functions to provide requested early response services using aircraft. However, the method can additionally or alternatively function to provide any suitable aircraft and/or vehicle-related services (e.g., emergency services, vehicle delivery services, personnel delivery services, product delivery services, etc.).

The method is preferably performed using an aerial vehicle system (e.g., the systems described in U.S. Provisional Application No. 62/452,051, titled "Systems and Methods for Providing Early Response Services", which is herein incorporated in its entirety by this reference). Although elements of the method are described as performed using an aircraft, a person of skill in the art will understand that the method (and optionally, any or all such elements of the method) can additionally or alternatively be performed using any other suitable system. For instance, the method can additionally or alternatively be performed using terrestrial vehicles (e.g., cars, road-going ambulances, etc.), amphibious vehicles, aquatic vehicles, space vehicles, or a combination of vehicle types.

2. Benefits

The system and/or method can confer several benefits. First, the system and/or method can enable autonomous operation of a vehicle or fleet of vehicles, which can reduce or eliminate the need for human presence on and/or operation of the vehicles. For example, a distribution of responsibilities (e.g., between humans and autonomous systems, between physical locations, etc.) can enable fewer human operators to efficiently perform necessary vehicle- and/or service-related tasks (e.g., for a fleet of vehicles) and/or increase safety, quality, and/or reliability by enabling human operators to concentrate on fewer tasks simultaneously (e.g., only one task at a time), while leveraging computer-based operation resources and/or autonomous control systems. For example, in some embodiments, a human operator can concentrate solely on selecting an appropriate landing site for an aircraft, while autonomous control systems handle safe, reliable, efficient control and navigation of the aircraft. This can facilitate providing fast, efficient, and/or safe vehicle-related services, such as air ambulance services, emergency response services, and/or transportation services.

Second, distribution of autonomous control systems can enable both sophisticated control requiring high-performance computing and communication, and safe control that is robust to issues such as communication failures and/or latency. For example, high-level control instructions can be generated and/or updated remotely (e.g., off-vehicle) and communicated to the vehicle, enabling high-level optimization of vehicle and fleet performance, while on-board systems can directly control the vehicle (e.g., based on the high-level control instructions and/or local sensor data), ensuring safe, consistent control throughout vehicle operation.

Third, providing the ability to accept and/or require inputs (e.g., confirmation inputs, abort inputs, etc.) from vehicle occupants (e.g., occupants not trained and/or licensed to operate the vehicle, passengers, etc.) can increase vehicle performance and/or help ensure safe vehicle operation. For example, the method can include requiring an occupant (e.g., non-pilot occupant) of a helicopter to confirm that a landing zone is clear before landing in the landing zone and/or allowing the occupant to indicate that flight conditions are too turbulent for safety and/or comfort. However, the system and/or method can additionally or alternatively confer any other suitable benefits.

3. Method

3.1 Receiving a Request for an Early Response Service

Receiving a request for an early response service S110 functions to receive information about a potential mission. The requested service can be an early response service (e.g., medical service, evacuation service, aerial firefighting service, survey and/or monitoring service, etc.), a non-emergent service (e.g., passenger and/or cargo transportation), and/or any other suitable service. The service request can be received from an emergency dispatch center (e.g., 911 call center), a user or potential user (e.g., user needing transportation, observer at an emergency scene, etc.), and/or from any other suitable requester. The request can be received by an aircraft, a ground-based control center (e.g., ground-based control center with human and/or non-human request processing entities), and/or any other suitable recipient.

The service request preferably includes waypoints (e.g., geographic locations, landmarks, other waypoints) associated with the service (e.g., pickup location, destination, etc.). The service request can additionally or alternatively include a priority classification (e.g., emergency, standard, low priority, etc.) and/or response time requirement (e.g., as soon as feasible; threshold time, such as 10 min, 20 min, 1 h, 4 h, etc.), a requested service type (e.g., medical emergency, such as heart attack, bleeding, burn, etc.; fire; crime; etc.) and/or requested service details (e.g., incident severity, patient medical history, etc.), additional information, such as areas to avoid (e.g., during aircraft flight, at a waypoint, etc.), other resources available (e.g., resources on scene and/or heading to the scene, etc.), other parties to coordinate with (e.g., other early responders, medical facilities, aircraft in the area, etc.), and/or any other suitable information. However, the request can be any suitable request received in any suitable manner.

3.2 Determining Mission Parameters Associated with the Request

Determining mission parameters associated with the request S120 functions to assess the request and the associated mission required to satisfy the request. S120 is preferably performed in response to receiving the request S110, but can additionally or alternatively be performed in response to any other suitable triggers and/or at any other suitable time. The mission parameters can include feasibility parameters, risk parameters, resource availability parameters, financial parameters, and/or any other suitable perimeters. In one example, the mission parameters can be represented as a mission parameters vector (e.g., ordered list of mission parameter values). However, the mission parameters can have any suitable representation.

Feasibility parameters can include location-related parameters (e.g., terrain, weather, visibility, daylight, elevation, etc.). In specific examples, terrain feature-associated parameters can include or otherwise be used to determine glide range aspects (e.g., glide ratio, glide slope, etc.) required for vehicles over given terrain. Feasibility parameters can additionally or alternatively include route-related parameters (e.g., travel time, fuel and/or battery charge requirements, other aircraft performance factors, airspace-related parameters, traffic-related parameters, etc.), patient condition-related parameters (e.g.; required, estimated, and/or ideal response time to reach a patient; patient transport considerations such as mechanical shock thresholds and/or noise thresholds; treatment considerations such as necessary, desired, and/or potentially useful equipment; triage considerations such as patient treatment/transport prioritization and/or patient transport destination determination; etc.), load parameters (e.g., weight, balance, etc.), and/or any other parameters related to the feasibility of satisfying the request. Risk parameters can include the risk of damage and/or loss (e.g., to aircraft, personnel, other resources, users, bystanders, other people and/or property, etc.), and/or any other parameters related to mission risk. In specific examples, such parameters can include requirements for vehicle travel about hazards, persons on the ground (e.g., in relation to congested areas, non-congested areas), obstacles, and any other suitable hazards. Resource availability parameters can include aircraft availability, personnel availability (e.g., medical personnel, etc.), and can include prioritization and/or triage parameters (e.g., that can allow comparison of different service requests and/or missions). The mission parameters can be determined based on the requests, based on additional information received from the requesting party, based on information received from other parties (e.g., emergency dispatch services, air traffic control services, other resources, etc.), based on information received from aircraft and/or personnel, and/or information from any other suitable source.

In a first example, the mission parameters are determined based on a projected worst-case scenario, and an additional safety factor is introduced to determine a conservative estimate of mission requirements. In a second example, the mission parameters are determined based on a projected likely scenario (e.g., typical scenario; worst scenario expected to typically occur in a length of time, such as a day, a week, a month, or a year; etc.). In a third example, a first set of parameters (e.g., including risk-related parameters and/or feasibility parameters) are determined based on a projected worst-case scenario, and a second set of parameters (e.g., including financial parameters) are determined based on a projected likely scenario. However, the mission parameters can include any suitable parameters, and can be determined in any suitable manner.

In other variations, mission parameters can be determined based on mission type. For instance, with missions involving an on-board medical professional (e.g., doctor, nurse, paramedic, emergency medical technician, etc.), the mission can include sequential flying to multiple waypoints rather than flights directly to a home base after each waypoint is reached. Alternatively (e.g., with missions not involving an on-board medical professional), the mission can include flights to a home base between each waypoint. However, mission parameters can additionally or alternatively be determined in any other suitable manner.

Furthermore, mission parameters can be determined based upon learnings from historical data acquired during previous missions. For instance, Block S120 can include retrieving actual responses/factors associated with environmental conditions, vehicle conditions, terrain conditions, and/or any other suitable conditions from previous vehicle operations (e.g., aircraft flights, terrestrial operations, etc.), in order to guide identification of mission parameters having similar aspects to previously conducted missions. In an example, a previous mission involving high terrain may have resulted in preparation of a flight path over the terrain at a specific altitude, but in practice, flight over the terrain at the altitude was unfavorable. Thus, identification of subsequent missions over high terrain may result in preparation of flight paths around the terrain to provide more favorable mission results.

Algorithms for processing historical data to guide future missions can be based on machine learning approaches. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminant analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolutional network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of machine learning algorithm.

3.3 Selecting Aircraft and/or Other Vehicle Types

Selecting aircraft S130 and/or other vehicle types functions to accept or decline the received request and to allocate resources to the associated mission. S130 preferably includes selecting aircraft to perform the mission, and can additionally or alternatively include selecting aircraft to support the mission, to compensate for coverage gaps (e.g., gaps created due to mission performance, etc.), and/or to select aircraft for any other suitable purpose. S130 can alternatively include selecting no aircraft and declining the service request (preferably communicating the decision to decline the service request to the requesting party and/or other parties associated with the request). Block S130 can include selecting a single aircraft for a single mission or multiple missions. Block S130 can additionally or alternatively include selecting multiple aircraft for a single mission or multiple missions. In multiple vehicle scenarios, the selected vehicles can include aircraft, terrestrial vehicles, and/or any other suitable vehicle type.

Aircraft and/or other vehicles are preferably selected S130 based on mission parameters, such as the parameters determined in S120, wherein aircraft/vehicles are preferably selected S130 concurrent with and/or after (e.g., in response to) determining the mission parameters S120. The aircraft can be selected based on location, aircraft and/or associated personnel capabilities, other service needs (e.g., concurrent missions, projected future needs, etc.), and/or any other suitable factors.

For example, aircraft (and/or other vehicles) can be selected based on a function of the mission parameters vector. In a specific example, a function of the mission parameters vector and of an aircraft parameters vector (e.g., representing information about an aircraft, about the aircraft fleet, etc.) can be used to select in the aircraft. In this specific example, each aircraft is associated with an aircraft parameters vector, and the aircraft whose aircraft parameters vector maximizes the function (for the given mission parameters vector) is selected (e.g., always selected based on maximizing the function; selected only if the function value exceeds a minimum threshold, wherein the service request can be declined if the function value does not exceed the threshold; etc.).

In a first variation, the closest aircraft (e.g., of the set of aircraft with appropriate resources to perform the mission) is selected. In this variation, aircraft distance can be determined based on geographical distance to the first waypoint (e.g., pickup location), estimated response time (e.g., response time to the first waypoint, response time to a subsequent time-sensitive waypoint, etc.), and/or any other suitable metric.

In a second variation, aircraft are selected to minimize the overall loss of coverage ability for the early response network. In this variation, aircraft can be selected from the set of all aircraft that can satisfy the mission requirements (e.g., estimated response time below a threshold value, having appropriate resources to perform the mission, etc.). In a specific example of this variation, in which a 20 minute response time is required for a mission, a first aircraft, located to the east of the pickup location, has a 10 minute projected response time, and a second and third aircraft, collocated to the west of the pickup location, each have a 15 minute projected response time. In this specific example, one of the two western aircraft is selected (despite their slower response time) in order to avoid creating a coverage gap in the eastern region.

In a third variation, aircraft can be selected to perform multiple concurrent (and/or consecutive) missions. The concurrent missions can include transporting multiple patients on departure and/or return routes. In a first example of this variation, after stabilizing an emergent patient, the aircraft can proceed to a second pickup location associated with a non-emergent mission (e.g., to pick up a stable patient, courier, passenger, cargo, etc.). In this example, the aircraft can then proceed to one or more drop-off locations (e.g., hospital, requested destination, etc.). In a second example, an aircraft that is currently performing a first mission (e.g., non-emergent mission, low-priority emergency mission, etc.) can be selected for an emergency mission (e.g., wherein the first mission is delayed in order to minimize response time for the emergency mission). In a third example, in which an aircraft is performing a first emergency mission, the aircraft can be selected (e.g., tentatively selected) for a second emergency mission (e.g., to be performed after completion of the first emergency mission, after time-sensitive steps of the first emergency mission, etc.). In this third example, the second emergency mission can optionally be reallocated to an alternative aircraft (e.g., in response to the first aircraft being delayed, the alternative aircraft becoming available earlier than anticipated, receipt of additional information such as changing weather and/or mission requirements, etc.).

In a fourth variation, an aircraft may be dispatched for a portion of a mission to deliver products to a terrestrial vehicle that completes the remainder of the mission. In a fifth variation, a terrestrial vehicle is selected rather than an aircraft (e.g., if the terrestrial vehicle is capable of completing the mission and would be more economical to use than an aircraft, if the terrestrial vehicle is expected to perform the mission more safely and/or effectively than an aircraft, etc.). However, the aircraft (and/or other vehicle) can be selected S130 in any other suitable way, based on any other suitable information, at any other suitable time.

3.4 Dispatching the Selected Aircraft and/or Other Vehicle Types

Dispatching the selected aircraft S140 and/or other vehicle types functions to initiate the mission. The aircraft are preferably dispatched S140 in response to selecting the aircraft S130 and/or other vehicle types, but can additionally or alternatively be dispatched at a predetermined time after the selection (e.g., for a non-emergent mission) and/or any other suitable time. Dispatching the aircraft S140 preferably includes performing preflight checks (e.g., safety checks of the selected aircraft) and sending a mission profile to the selected aircraft, and can additionally or alternatively include any other suitable elements.

Performing preflight checks functions to ensure that the aircraft is safe for flight and ready to carry out the mission. The preflight checks can be performed using sensors onboard the aircraft (e.g., aerial vehicle diagnostic systems), external sensors near the aircraft (e.g., at a landing and/or storage location occupied by the aircraft), and/or sensors of any suitable system in any suitable location. The sensors can include optical sensors (e.g., cameras), sonar, heat sensors, and/or any other suitable sensors. Performing preflight checks can additionally or alternatively be implemented with a human examiner or other entity according to a checklist.

Sending the mission profile to the aircraft functions to communicate information associated with the mission to the aircraft. The mission profile can include one or more waypoints (e.g., first waypoint, all waypoints, etc.), locations, desired paths (e.g., for path following), and/or desired velocities (e.g., with direct velocity commands). The mission profile can additionally or alternatively include additional information from the service request, mission parameters (e.g., determined in S120), other selected and/or available aircraft (e.g., along with information about these additional aircraft, such as capabilities, locations, intended roles, etc.), and/or supplemental information. The supplemental information can include maps (e.g., terrain, radar, visual flight rules maps, instrument flight rules maps, other airspace factors, etc.), weather conditions and/or forecasts (e.g., visibility, winds, moisture, density, altitude, etc.), air traffic information (e.g., notices to airmen, temporary flight restrictions, alerts, information related to special use areas, global and/or local obstacle information, right-of-way rules, traffic advisories, etc.), noise abatement and/or ground congestion information (e.g., population density, noise burden, public gatherings, etc.), resource information (e.g., location and/or availability of mission-critical and/or potentially useful resources such as medicine, equipment, etc.), and/or any other suitable information. However, the selected aircraft can be dispatched in any other suitable manner.

3.5 Controlling Dispatched Aircraft Flight and/or Vehicle Operation

Controlling aircraft flight S150 and/or other vehicle operation functions to control the vehicle(s) to perform the mission. Aircraft flight is preferably controlled S150 in response to aircraft dispatching S140 (e.g., wherein the aircraft is controlled to take off and perform the mission upon being dispatched), but can additionally or alternatively be controlled at any other suitable time.

The aircraft is preferably autonomously controlled, but can additionally or alternatively be manually controlled. Autonomous aircraft flight can be completely autonomous (e.g., without human entity involvement; performed entirely by on-board systems, performed in part or all by remote systems such as automated air traffic control systems, etc.), or can allow and/or require human and/or other external inputs (e.g., from ground station personnel, on-board personnel, requesting users, etc.). For example, human and/or external inputs can be used to modify the mission (e.g., flight path, landing location, etc.), trigger evasive maneuvers (e.g., to avoid collision with incoming air traffic and/or other obstacles), trigger contingency maneuvers (e.g., due to off-nominal flight conditions, such as motor failure, chassis damage, low fuel, extreme weather, etc.), directly control the aircraft, and/or modify aircraft flight in any other suitable way. Contingency maneuvers can include course alterations, speed alterations, expedited landing (e.g., land at nearest ground station, land at nearest known helipad, runway, and/or other regular landing location, land at an emergency site, immediately begin landing, etc.), safety system deployment, and/or any other suitable maneuvers. Direct aircraft control can be limited and/or unlimited (e.g., determined based on mission stage, aircraft status, controller qualifications, etc.). In a specific example, personnel on-board the aircraft can directly control aircraft horizontal alignment and descent rate during a landing procedure (e.g., in a standard operation mode, or in an override mode).

The aircraft is preferably controlled based on the mission parameters (e.g., determined as described above regarding S120). The mission parameters on which aircraft control is based can be determined prior to aircraft selection, determined during mission performance (e.g., based on information received from observers, inputs received from aircraft personnel such as medical professionals, sensor measurements such as patient condition sensors and/or aircraft sensors, communications from ATC and/or other aircraft, etc.). In one variation, the aircraft is controlled based on patient condition-related parameters, such as patient transport considerations. In a first example of this variation, a patient on the aircraft urgently needs advanced medical treatment (e.g., available at a hospital but not onboard the aircraft). In this example, the aircraft can be controlled to fly to and land at a hospital (e.g., the closest acceptable hospital) quickly (e.g., as quickly as possible, practical, and/or safe).

In a second example of this variation, a patient on the aircraft is in a stable condition (e.g., not deteriorating, not in urgent need of medical care beyond that provided in the aircraft) but has potentially suffered a spinal injury (e.g., shows signs of a spinal injury, has injuries and/or symptoms consistent with a spinal injury, was observed to undergo a trauma that could cause a spinal injury, etc.). In this example, the aircraft can be controlled to attempt to minimize the mechanical shock exerted on the patient (e.g., to reduce the likelihood of spinal injury exacerbation). For example, the aircraft can be flown at a reduced velocity; can be navigated around regions of atmospheric turbulence; and/or can be routed toward a destination selected based on a number of factors (e.g., not based solely or primarily on minimizing transport time to the destination), such as distance, intervening weather conditions, care availability at the destinations, transport costs, patient preferences, and/or any other suitable factors.

In a third example of this variation, the aircraft has not yet reached the patient location. In a first specific example, in which the patient is possibly in urgent need of medical treatment (e.g., is bleeding rapidly, is unconscious, etc.), the aircraft can be controlled to fly toward and land near the patient quickly (e.g., as quickly as possible, practical, and/or safe). In a second specific example, in which the patient is not in urgent need of medical treatment (e.g., has broken a bone, necessitating helicopter evacuation, but is in a stable condition), the aircraft can be controlled to fly based on economic (e.g., minimizing fuel consumption) and/or safety considerations. This example can additionally or alternatively include determining the aircraft landing location based on the patient condition-related parameters. For example, if the patient condition precludes significant patient movement on the ground, a landing location can be selected to reduce (e.g., minimize) the distance between the patient and the aircraft, whereas if the patient can be safely and easily moved, a landing location farther from the patient can be selected if it is preferable based on other considerations (e.g., increased safety of landing at the location, lesser incline angle of the landing location, etc.). However, the aircraft can additionally or alternatively be controlled based on any other suitable parameters.

3.5.1 Distributed Aircraft Control.

Controlling aircraft flight S150 preferably includes aviating, navigating, and communicating. Aircraft flight control responsibilities (e.g., aviation, navigation, communication, etc.) can be performed exclusively by on-board aircraft systems, can be distributed between systems in multiple locations (e.g., on-board aircraft systems, ground station systems, other aircraft, etc.), and/or can be performed by any other suitable system(s).

Aviating functions to control the aircraft to maintain safe flight conditions, and preferably functions to follow the mission plan. Aviating preferably includes generating state data and/or controlling aircraft systems.

Navigating can function to determine the aircraft route and/or plans (e.g., heuristics) for updating the route based on new information. Navigating can include determining (and/or updating) a mission plan based on currently-available information (e.g., from aircraft sensors, external data, etc.). In a first variation, the mission plan is generated by a human operator. In a second variation, the mission plan is generated by machine learning processes (e.g., reinforcement learning, Markov and/or partially observable Markov decision processes, etc.), and can optionally be reviewed by a human operator after generation. The mission plan can be represented as a neural network, a sequence of maneuvers, a Markov control policy, and/or can have any other suitable representation.

Communicating can function to disseminate updated information to the aircraft and/or network, facilitate coordination with other parties, and/or satisfy regulatory requirements (e.g., air traffic control requirements). Communication is preferably performed via radio (e.g., audio transmission, transponder, LTE, satellite, etc.), but can additionally or alternatively be performed using any other suitable communication modules. The aircraft is preferably controlled to communicate with air traffic control and/or other aircraft (e.g., via voice communication, using ADS-B systems to observe locations and tracks of other aircraft, etc.), and can additionally or alternatively be controlled to communicate with emergency responders and/or other resources, users, ground stations (e.g., ground stations manned by human entities, by non-human entities, etc.), auxiliary data sources (e.g., weather information sources, etc.), medical treatment centers (e.g., hospitals, etc.) and/or other potential aircraft destinations (e.g., pickup and/or dropoff locations, etc.), and/or any other suitable endpoints. The aircraft can send and/or receive telemetry, mission plans (e.g., updated based on new information and/or analysis), auxiliary data, control commands, mission-related information (e.g., patient health condition), and/or any other suitable information. Aircraft communications can be performed directly between the aircraft and the communication endpoints, and/or can be relayed (e.g., through ground stations, other aircraft, etc.). In a first variation, the communications are directly relayed. In a second variation, the communications are translated and/or augmented by a relayer. For example, ground station personnel can perform voice communication with the communication endpoints (e.g., air traffic control, first responders, etc.), and can communicate with the aircraft via a computerized data transmission to transmit and receive substantive information (e.g., information related to the voice communications, such as encodings of the information communicated, data needed to respond to queries from the communication endpoints, etc.).

State data is preferably generated based on aircraft sensors (e.g., optical cameras, ultrasonic sensors, radar, lidar, temperature sensors, altimeters, accelerometers, gyroscopes, magnetometers, barometers, GPS receivers, etc.), but can additionally or alternatively be generated based on external sensors (e.g., ground station sensors, sensors of other aircraft, etc.), information received from other parties, and/or any other suitable information. State data can include aircraft position and/or orientation (and/or rates of change thereof), external observables, and/or any other suitable data types. State data can be determined based on raw sensor data, filtered and/or analyzed sensor data (e.g., using Kalman filter, classification, heuristics, etc.).

The aircraft systems are preferably controlled (e.g., by a control system) based on the state data. Aircraft systems to be controlled can include power systems (e.g., motors), control surfaces, safety systems, and/or any other suitable systems. In one example, in which the aircraft is a helicopter, the controls can include cyclic control, collective pitch control, tail rotor blade pitch control, and throttle. In a second example, in which the aircraft is an airplane, the controls can include one or more of: aileron control, elevator control, rudder control, throttle control, propeller pitch control, flap control, landing gear control, and any other suitable airplane control. In a third example, in which the method is performed using a wheeled terrestrial vehicle, the controls can include one or more of: wheel steering angle control, brake control, gas vs. electric engine operation control, throttle control, and any other suitable wheeled terrestrial vehicle control. The systems can be controlled using one or more different methods in combination or isolation, such as rule-based systems, methods from control theory such as Proportional-Integral-Derivative and Linear Quadratic Register, control policies for Markov Decision Processes or Partially Observable Markov Decision Processes, and/or any other suitable methods. The control methods can be employed using predefined parameters and/or using dynamically modified parameters (e.g., modified based on the mission profile, modified by machine learning methods, etc.). The control system may communicate with the actuators and other like devices using analog and digital methods such as Pulse Width Modulation, Serial Commands, Voltage Control, and Current Control. The aircraft systems can additionally or alternatively by controlled based on human control inputs (e.g., overriding automated control, informing motorized control of aircraft systems, directly controlling aircraft systems such as through mechanical linkages, etc.). However, the aircraft systems can be controlled in any other suitable manner.

Figure 2A:
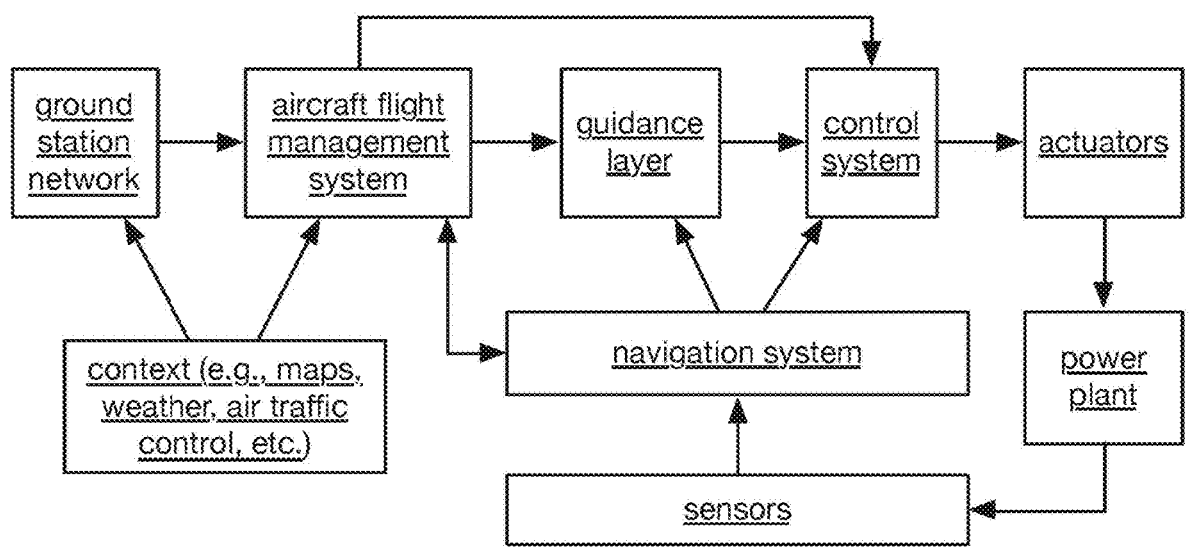
FIG. 2A is a schematic representation of a specific example of distributed control systems for performing the method.
Figure 2B:
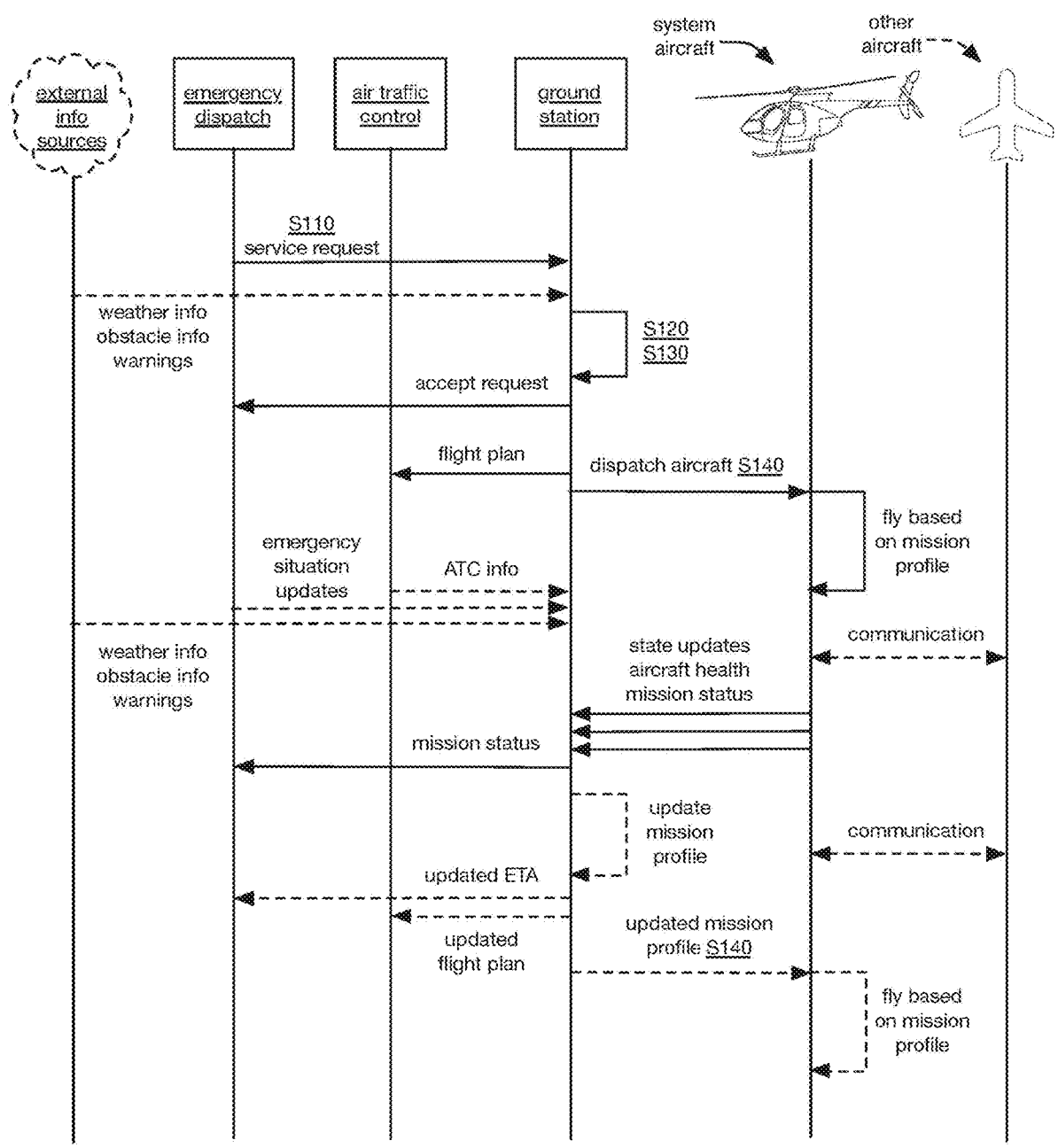
FIG. 2B is a schematic representation of a specific example of the method.

In a specific example (e.g., as shown in FIGS. 2A-2B), aircraft flight control is distributed between a ground station network and several systems on-board the aircraft, including an aircraft flight management system, navigation system, guidance layer, and control system. In this specific example, the ground station network generates an initial mission profile and relays communications to the aircraft, and can optionally perform computations related to aircraft control (e.g., determining flight trajectories, landing locations, etc.). The navigation system consumes raw sensor data and processes them to resolve the state of the aircraft and the world, generating aircraft state data which is made available to the Aircraft Flight Management, Guidance, and Control systems. The aircraft flight management system receives the initial mission profile and relayed communications from the ground station network, receives aircraft state data from the navigation system, and determines updated mission plans based on the new information it receives. The guidance layer receives updated mission plans from the aircraft flight management system and receives aircraft state data from the navigation system, determines a series of maneuvers (e.g., high level directives such as takeoff, fly to waypoint, land, etc., which can be associated with locations and/or any other suitable information; control policy for a Markov Decision Process or Partially Observable Markov Decision Process; etc.) based on the received information, and emits commands to the control system to accomplish these maneuvers, based on the current state values. The control system generates control signals based on the commands received from the guidance layer and state data received from the navigation system, and transmits the control signals to the actuators in order to actuate the aircraft control systems.

3.5.2 Landing the Aircraft.

Figure 4A:
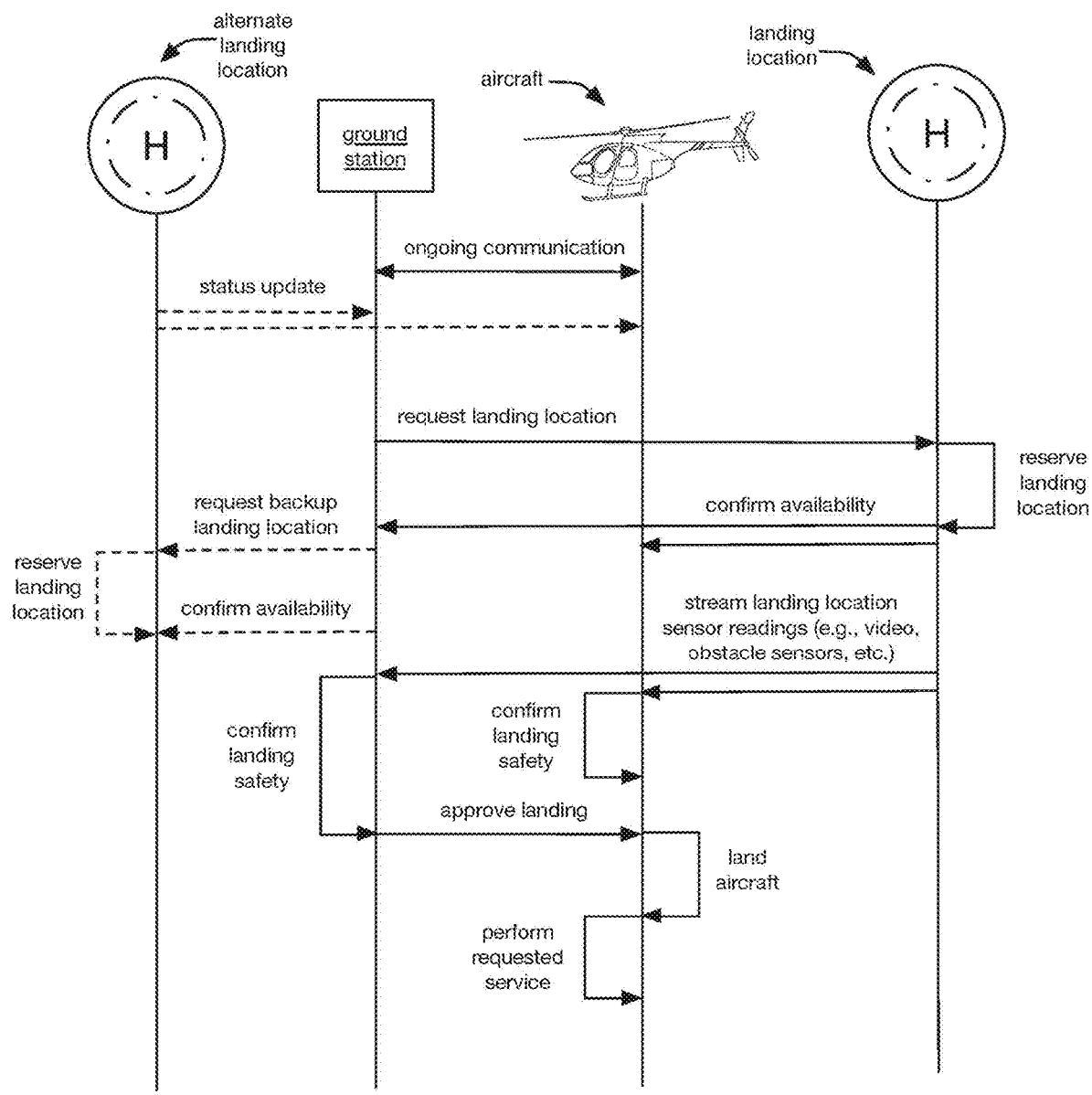
FIGS. 4A-4B are schematic representations of a first and second specific example of landing the aircraft, respectively.
Figure 4B:
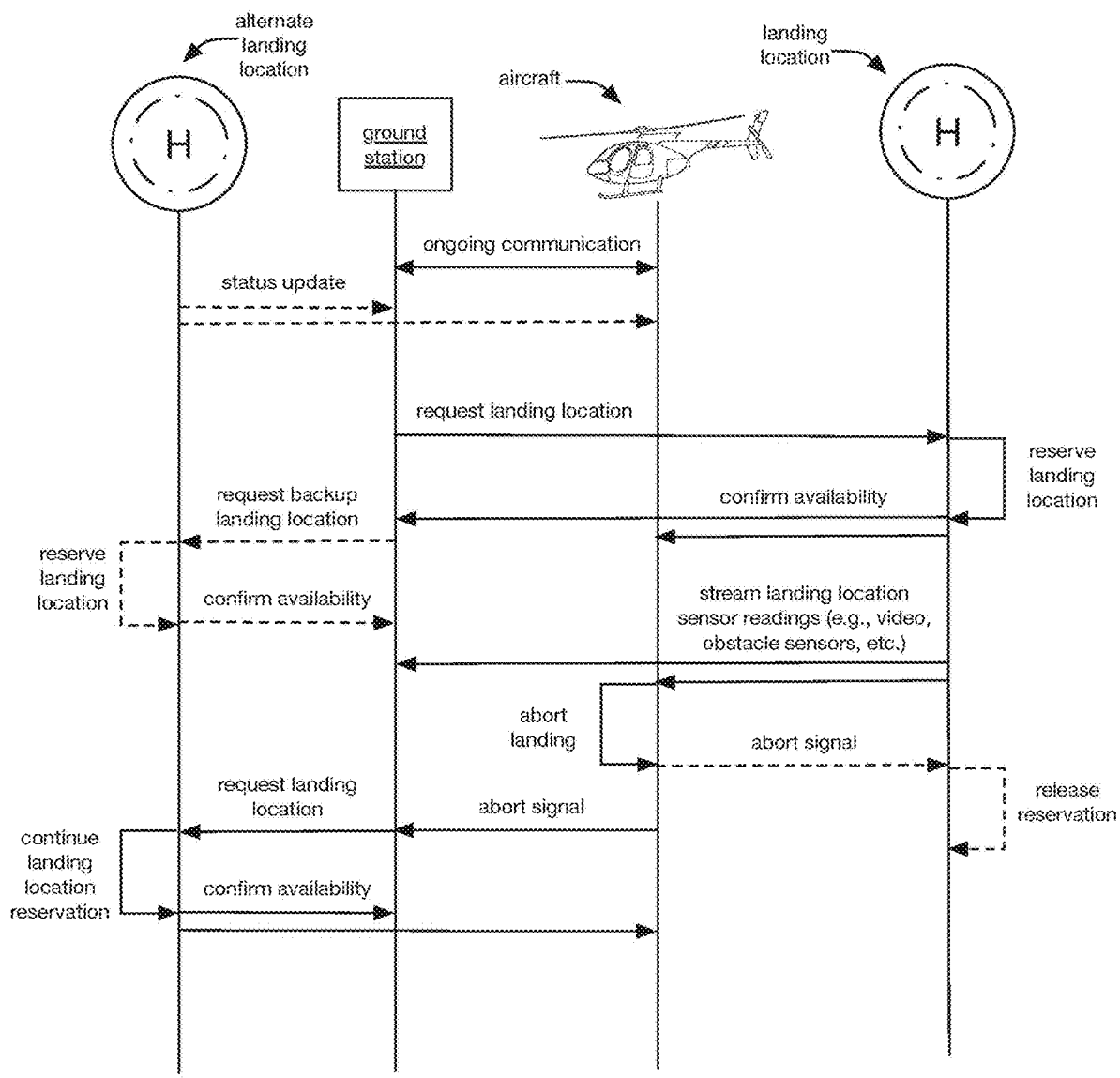

Controlling aircraft flight S150 preferably includes controlling the aircraft to land (e.g., as shown in FIGS. 4A-4B). The aircraft can be controlled to land in response to reaching a landing waypoint (e.g., pickup and/or drop-off location, ground station, etc.), in response to off-nominal flight conditions, in response to receipt of a directive to land, in response to any other suitable trigger, and/or at any other suitable time. Controlling the aircraft to land can include determining that a landing is safe, outputting a landing warning, and performing the landing.

A landing is preferably determined to be safe in an autonomous manner. A human (e.g., on-board personnel, ground station personnel, observer near a landing location, etc.) can additionally or alternatively authorize and/or abort the landing (e.g., determine the landing is safe or not safe). Landing safety can be determined based on sensor measurements (e.g., on-board aircraft sensors, landing site sensors, etc.), visual inspection, and/or any other suitable information. Landing safety can be determined based on landing location status (e.g., terrain, damage, obstructions, etc.), aircraft status, environmental status (e.g., visibility, air density, etc.), and/or any other suitable factors. In some variations, a threshold for landing safety determination (e.g., safety threshold value to be exceeded in order to determine that a landing is safe) can be dynamically adjusted based on other factors (e.g., mission urgency, landing urgency, alternative landing options, aircraft status, etc.). For example, a safety threshold for an urgent mission landing can be lower than for a non-emergent mission, but higher than for an emergency landing during aircraft system failure. If the landing is determined to not be safe, the aircraft can wait for the landing to become safe (e.g., hover near the landing location until obstacles on the platform are cleared) and/or proceed to an alternative landing location (e.g., based on instructions from the ground station network).

A landing warning is preferably output throughout the landing process (e.g., during landing safety determination and/or landing performance), but can additionally or alternatively be output at any other suitable time. The landing warning can include visual warnings (e.g., flashing lights, projection onto ground indicating the landing location, etc.), audible warnings (e.g., spoken warnings, klaxons, etc.), and/or any other suitable warnings. The warnings can be output by output modules of the aircraft, output modules of the landing location, and/or any other suitable output modules.

The landing is preferably performed in response to determining the landing is safe and concurrent with outputting the landing warning, but can additionally or alternatively be performed at any other suitable time. The landing can be performed by controlling aircraft flight autonomously (e.g., as described above) and/or in any other suitable manner.

Figure 3:
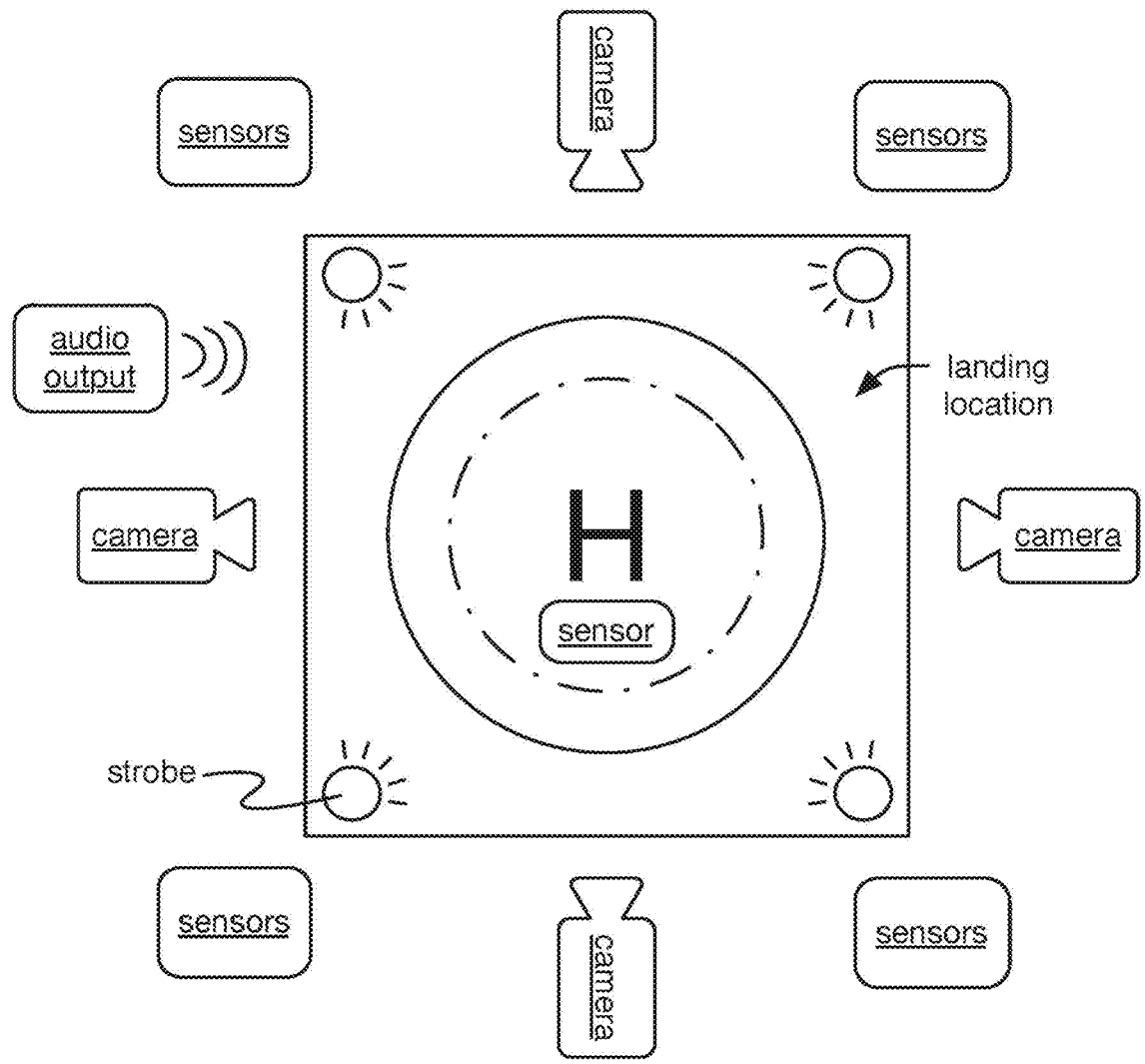
FIG. 3 is a perspective view of a specific example of a landing location.

In a first variation, in which the aircraft lands at a dedicated landing location (e.g., ground station; example shown in FIG. 3), sensors of both the aircraft and the landing location can be used to determine landing safety, and output modules of both the aircraft and the landing location can be used to output the landing warning. In a second variation, the aircraft lands at a location that is not dedicated to autonomous aircraft landing (e.g., standard helipad, medical evacuation site, emergency landing site, etc.). In this variation, the aircraft can act alone to determine landing safety and output landing warnings. However, controlling the aircraft to land can include any other suitable elements, and aircraft flight can be controlled in any other suitable manner.

3.6 Performing a Service at a Waypoint

Performing a service at a waypoint S160 can function to satisfy mission requirements. The service is preferably performed in response to aircraft arrival at the waypoint (e.g., upon landing at the waypoint, upon establishing a hovering position above the waypoint, etc.), but can additionally or alternatively be performed at any other suitable time. Performing the service can include cargo and/or passenger loading and/or unloading (e.g., allowing passengers to embark/disembark, loading and securing a patient for transport to a hospital, etc.), performing medical treatment (e.g., stabilizing a patient, etc.), performing surveillance, releasing a fire extinguishing agent, and/or performing any other suitable services.

In a first variation, the aircraft lands before performing the service (e.g., and subsequently takes off after performing the service), which can enable easy ingress and/or egress. In a second variation, the aircraft does not land (e.g., hovers above the waypoint). In a first example of this variation, on-board personnel (e.g., medical personnel) can exit the aircraft while it hovers (e.g., using a rope, hoist, parachute, etc.). In this example, after exiting the aircraft, the personnel can perform the service on the ground (e.g., perform medical treatment) and/or can retrieve an injured person on the ground (e.g., wherein the injured person and/or medical personnel are subsequently hoisted into the aircraft). However, the service can be performed in any other suitable manner.

After performing the service, the aircraft can continue to perform the mission (e.g., continue to the next waypoint), can be dispatched for a new mission, can return to a ground station (e.g., its original the ground station), can remain at its current location, can repeat any or all elements of the method, and/or can perform any other suitable actions.

3.7 Specific Example

In a specific example of the method, the ground station network (GSN) learns of an incident from an emergency dispatcher (e.g., emergency medical dispatcher, 911 dispatcher) and/or through direct contact with a bystander. The GSN chooses the appropriate vehicle, given parameters such as the distance from the incident, equipment on site, current weather conditions, obstacles on the way and other safety considerations. A formal risk assessment is conducted as well, ensuring that the proposed mission complies with laws, regulations, and policies of Federal, State, and Local government and other relevant entities. The mission is then generated and uploaded to the dispatched vehicle, and the first responders at the dispatch site are informed of their mission.

The motor starts spinning as soon as the mission is uploaded, to allow it to heat up. Before takeoff, final visual inspection is conducted (e.g., via cameras and/or other sensors on site, by personnel on site, etc.), and additional pre-flight checks can additionally or alternatively be performed (e.g., via sensors of the aircraft, external sensors, personnel on site, etc.). The GSN informs air traffic control of the critical rescue mission and continues sending updates. The vehicle takes off and starts to perform the mission. Warning signals (e.g., blinking lights, sirens, landing zone projection, etc.) can be activated at the dedicated landing location in order to warn people in the vicinity and clear the landing area.

While the vehicle is in the air, the GSN is informed by 911 dispatch about updates on the patient condition. This information is communicated to the first responder on board of the vehicle. Upon vehicle arrival near the landing location, the GSN, Aircraft Flight Management System, and the first responder on board the vehicle observe the landing location via appropriate sensors. In case of any unexpected disturbances, the landing can be halted or aborted and an alternative landing spot chosen.

Once the vehicle has landed, the first responder exits the aircraft and begins treating the patient. After the patient has been treated, the first responder returns to the vehicle, a return-to-base mission is created, similarly to the mission explained above. If the return mission is not considered critical (e.g., if the vehicle is not performing an EMS mission), more communication between GSN and air traffic control can be necessary (e.g., in order to re-route the vehicle as instructed). Communications from air traffic control (e.g., instructions, advisories, requests, etc.) are consumed by the GSN, which can modify and update the mission accordingly, preferably transmitting the updates to the vehicle. Additionally or alternatively, communications from air traffic control can be consumed by the vehicle itself (e.g., should the need arise, such as due to a communication failure between the vehicle and the GSN).

The vehicle reaches home and lands. Required and/or desired reports and/or logs (e.g., Patient Care Reports, etc.) are automatically generated (e.g., based on the mission plan and/or vehicle status during the mission), and are preferably verified by the first responder and/or the GSN (e.g., before submission). Critical data (e.g., location, time of arrival, etc.) can be automatically obtained using various sensors (e.g., vehicle sensors, such as sensors on top of the vehicle). The vehicle can be refueled and restocked (e.g., to be readied for a subsequent mission) autonomously and/or manually. Post-flight inspections can optionally be performed (e.g., as described above regarding pre-flight visual inspection and/or other checks). However, the method can be performed in any suitable manner.

Although omitted for conciseness, the preferred embodiments include every combination and permutation of the various system components and the various method processes. Furthermore, various processes of the preferred method can be embodied and/or implemented at least in part as a machine configured to receive a computer-readable medium storing computer-readable instructions. The instructions are preferably executed by computer-executable components preferably integrated with the system. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processing subsystem, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:
1. A method comprising:
  receiving a service request associated with patient located at a patient location;
  determining mission parameters for controlling a vehicle to move to a region including the patient location;
  controlling the vehicle to move to the region based on the mission parameters;

receiving a condition parameter of the patient, the condition parameter indicating at least one of: a medical condition of the patient or a medical treatment to be applied to the patient;

determining a destination, based on the condition parameter of the patient, for the vehicle to move to after the patient is in the vehicle; and responsive to the vehicle arriving at the region and responsive to receiving an indication that the patient is in the vehicle, autonomously controlling the vehicle, based on the condition parameter of the patient, to move to the destination.

2. The method of claim 1, wherein determining the destination is further based on at least one of: distance between the patient location and the destination, weather conditions between the patient location and the destination, care availability at the destination, transportation costs, or patient preferences.

3. The method of claim 1, wherein the destination is the closest medical facility to the patient location that can provide the medical treatment associated with the condition parameter of the patient.

4. The method of claim 1, wherein controlling the vehicle based on the condition parameter of the patient comprises controlling a parameter of the vehicle based on the condition parameter of the patient.

5. The method of claim 4, further comprising:
determining that the medical treatment for the patient is not available on the vehicle.

6. The method of claim 5, further comprising:
responsive to determining that the medical treatment for the patient is not available on the vehicle, adjusting the parameter of the vehicle to decreases a travel time to arrive at the destination.

7. The method of claim 1, wherein controlling the vehicle based on the condition parameter comprises controlling the vehicle to reduce mechanical shock below a threshold value.

8. The method of claim 1, wherein controlling the vehicle based on the condition parameter comprises controlling the vehicle to reduce a velocity of the vehicle below a threshold value.

9. The method of claim 1, wherein the vehicle is an aircraft and controlling the vehicle based on the condition parameter comprises controlling the vehicle to navigate around an area with atmospheric turbulence.

10. The method of claim 1, wherein the vehicle is an aircraft and the method further comprises determining a landing location in the region based on the condition parameter of the patient.

11. The method of claim 10, wherein determining the landing location based on the condition parameter of the patient comprises:
responsive to the condition parameter of the patient indicating that the patient is in urgent need of medical treatment, determining the landing location with the shortest distance to the patient location.

12. The method of claim 10, wherein determining the landing location based on the condition parameter of the patient comprises:
responsive to the condition parameter of the patient indicating that the patient is immobile or indicating that mobility of the patient is limited to a threshold distance, determining the landing location with the shortest distance to the patient location.

13. The method of claim 10, wherein determining the landing location is further based on sensor measurements from on-board aircraft sensors.

14. The method of claim 1, wherein the mission parameters are generated by a machine learned process.

15. The method of claim 14, wherein the machine learned process is trained based on historical data acquired during previous missions that responded to previous service requests.

16. The method of claim 1, wherein the vehicle is an aircraft.

17. The method of claim 1, wherein the vehicle is a terrestrial vehicle.

18. A non-transitory computer-readable storage medium comprising stored instructions, the instructions, when executed by a computing device, cause the computing device to perform operations including:
receiving a service request associated with patient located at a patient location;
determining mission parameters for controlling a vehicle to move to a region including the patient location;
controlling the vehicle to move to the region based on the mission parameters;
receiving a condition parameter of the patient, the condition parameter indicating at least one of: a medical condition of the patient or a medical treatment to be applied to the patient;
determining a destination, based on the condition parameter of the patient, for the vehicle to move to after the patient is in the vehicle; and
responsive to the vehicle arriving at the region and responsive to receiving an indication that the patient is in the vehicle, autonomously controlling the vehicle, based on the condition parameter of the patient, to move to the destination.

19. A system comprising:
a computing device; and
a computer-readable storage medium comprising stored instructions, the instructions, when executed by the computing device, cause the computing device to perform operations including:
receiving a service request associated with patient located at a patient location;
determining mission parameters for controlling a vehicle to move to a region including the patient location;
controlling the vehicle to move to the region based on the mission parameters;
receiving a condition parameter of the patient, the condition parameter indicating at least one of: a medical condition of the patient or a medical treatment to be applied to the patient;
determining a destination, based on the condition parameter of the patient, for the vehicle to move to after the patient is in the vehicle; and
responsive to the vehicle arriving at the region and responsive to receiving an indication that the patient is in the vehicle, autonomously controlling the vehicle, based on the condition parameter of the patient, to move to the destination.

20. The non-transitory computer-readable storage medium of claim 19, wherein the vehicle is an aircraft and the operations further include determining a landing location in the region based on the condition parameter of the patient.

\* \* \* \* \*

UNITED STATES PATENT AND TRADEMARK OFFICE
CERTIFICATE OF CORRECTION

| | |
|---|---|
| PATENT NO. | : 11,921,507 B2 |
| APPLICATION NO. | : 17/551595 |
| DATED | : March 5, 2024 |
| INVENTOR(S) | : Groden et al. |

It is certified that error appears in the above-identified patent and that said Letters Patent is hereby corrected as shown below:

In the Claims

In Column 16, in Claim 20, Line 61, delete "claim 19," and insert -- claim 18, --, therefor.

Signed and Sealed this
Eleventh Day of June, 2024

Katherine Kelly Vidal
*Director of the United States Patent and Trademark Office*